United States Patent [19]

Grollier

[11] Patent Number: 4,892,727

[45] Date of Patent: Jan. 9, 1990

[54] COSMETIC OR DERMOPHARMACEUTICAL COMPOSITIONS CONTAINING A POWDER OF SWEET LUPINE SEEDS ESSENTIALLY FREE OF ALKALOIDS

[75] Inventor: Jean-François Grollier, Paris, France

[73] Assignee: Societe Anonyme dite: L'OREAL, Paris, France

[21] Appl. No.: 889,001

[22] Filed: Jul. 24, 1986

[30] Foreign Application Priority Data

Jul. 24, 1985 [LU] Luxembourg ............................ 86021

[51] Int. Cl.⁴ ........................ A61K 7/02; A61K 7/027; A61K 7/035; A61K 7/06
[52] U.S. Cl. .......................................... 424/69; 8/161; 252/106; 424/DIG. 5; 424/61; 424/63; 424/64; 424/65; 424/68; 424/70; 514/844; 514/845; 514/846; 514/847; 514/937; 514/944; 514/949; 514/969
[58] Field of Search ...................... 424/59, 60, 65, 69; 260/412.4

[56] References Cited

U.S. PATENT DOCUMENTS 2,615,905 10/1952 Heinrich et al. ............. 260/412.4 X
4,170,638 10/1979 Owades .................................. 424/65
4,460,488 7/1984 Grollier et al. ........................ 424/64

FOREIGN PATENT DOCUMENTS 2067899 8/1981 United Kingdom .................. 424/20

OTHER PUBLICATIONS (Schmid) List, Hagers Handbuch Der Pharmazeutischen Praxis, 1976, p. 590.
Steinmetz, Codex Vegetabilis, 1957, #676.
Lewis, Medical Botany Plants Affecting Man's Health, p. 17, 44, 82, 93, 110 and 219, 1977.
Martindale, The Extra Pharmacopeia, vol. I, p. 683.

Primary Examiner—Dale R. Ore
Attorney, Agent, or Firm—Cushman, Darby & Cushman

[57] ABSTRACT

A cosmetic or dermopharmaceutical composition comprises in an appropriate support or vehicle, a powder of sweet lupine seeds essentially free of alkaloids.

10 Claims, No Drawings

COSMETIC OR DERMOPHARMACEUTICAL COMPOSITIONS CONTAINING A POWDER OF SWEET LUPINE SEEDS ESSENTIALLY FREE OF ALKALOIDS

The present invention relates to a new composition for application to the skin, the hair and the scalp, the said composition containing a powder of sweet lupine seeds.

It is known that the cosmetic and dermopharmaceutical industry uses numerous substances in the formulation of compositions intended for cleansing and treating the skin and hair, as well as compositions for caring for and improving the skin and hair.

In the preparation of these cosmetic or dermopharmaceutical compositions, various synthetic or semi-synthetic adjuvants have been proposed. Currently, however more and more emphasis is being placed on the use of natural products, and in particular, vegetable substances.

The applicaants have now discovered that the use of a powder of lupine seeds provides the production of cosmetic or dermopharmaceutical compositions which exhibit interesting and useful properties.

The composition of the present invention comprises, in an appropriate vehicle or support a powder of sweet lupine seeds which are essentially free of alkaloids.

It is known that the seeds of numerous varieties of lupine contain alkaloids. However, it is also known that certain varieties of selected lupines, termed "sweet lupine", are practically free of alkaloids. It is these latter seeds that are employed in the present invention. Representative ones of such "sweet lupines" include the following varieties: *Lupinus albus* (white lupine), *Lupinus angustifolius, Lupinus polyphyllus,* and *Lupinus luteus.*

The four above mentioned species contain alkaloids in an amount lower than 0.3 weight percent.

The present invention thus relates to a composition for application to the skin, the hair and the scalp, comprising in a vehicle suitable for application to the hair or skin at least 0.5 percent by weight, based on the total weight of the composition, of a powder of sweet lupine seeds essentially free of alkaloids. The said powder generally has a granulometry lower than or equal to 125 µm.

The support or vehicle is preferably an aqueous support.

The powder of the sweet lupine seeds employed in accordance with the present invention is obtained by simply crushing the seeds in a conventional grinder, followed by sifting or screening the said crushed or ground seeds to produce a fraction having the desired granulometry.

Preferably, the powder of the sweet lupine seeds employed in the compositions of the present invention is such that at least 98% of the particles have dimensions lower than 80 µm.

When the compositions of the present invention are intended for the treatment of oily skin or oily hair thereby taking advantage of the absorption properties of the powdered lupine seeds, the said powder can be prepared from delipidated seeds. This delipidation treatment comprises, for example, extracting the fatty bodies of the seeds with an organic solvent. This treatment, when it is applied to the seeds, also improves the grinding of the seeds.

The applicants have discovered that the incorporation of the powder of sweet lupine seeds in cosmetic or dermopharmaceutical compositions provides an unctuous, creamy and homogeneous composition, the application of which to the hair or skin is both easy and agreeable.

In particular, the powder of sweet lupine seeds is easily incorporated in oily vehicles as well as in aqueous vehicles so as to produce compositions in the form of emulsions or gels. The resulting homogeneous and smooth emulsions exhibit a high capacity for oil and water absorptions. The powder of sweet lupine seeds is particularly well adapted for the preparation of cosmetic emulsions for the skin, the scalp and the hair, such as shampoos, after-shampoo compositions, or rinses, make-up emulsions and creams, lipstick, make-up formulations, emulsions for the care of the body, depilatory or deodorant compositions, cleansing compositions or compositions for the care of the hands, bath preparations, make-up removal compositions and the like. These emulsions which are smooth, unctuous and homogeneous can be removed in a satisfactory manner with water.

The compositions according to the present invention, in the form of emulsions, include generally from 0.5 to 15 weight percent of the powder of sweet lupine seeds relative to the total weight of the composition.

The powder of sweet lupine seeds also permits the preparation of absorbent cosmetic compositions, in the form of powders of "talcs" for the body, such as antiperspirant and deodorizing powder, or even in the form of dry shampoo compositions.

In these compositions, in the form of powders, the amount of the powder of sweet lupine seeds, relative to the total weight of the composition, can exceed 35 weight percent, especially in the case of make-up powders.

The powder of sweet lupine seeds can also be employed in cosmetic compositions in the form of gels having a thick consistency such as, for example, face masks, dipilatory masks, deodorant sticks, eyelid make-up sticks and the like.

It has been observed that notwithstanding their thick consistency, such compositions are easily spreadable. After application of the composition in the form of masks, the skin is soft and velvety to the touch.

In such gel form compositions having a thick consistency, the powder of the sweet lupine seeds is generally present in amount ranging from 0.5 to 35 percent by weight, relative to the total weight of the composition.

The pH of these compositions generally ranges from 4 to 10 and preferably from 5.5 and 8.

In a general manner, the cosmetic compositions according to the present invention exhibit interesting and useful properties.

For example, it has been observed that capillary compositions according to the present invention are particularly favorable in the treatment and care of fine and soft hair, whether it be natural hair or hair sensitized by treatments such as dyeing, bleaching, or permanent deformation operations. The composition of the present invention imparts to such hair particularly interesting holding qualities. Moreover, the compositions of the present invention impart liveliness to the hair and at the same time improve its appearance and render it supple, lustrous, soft and manageable. These compositions also facilitate combing and styling the hair and impart shininess and fullness thereto. These compositions also improve the holding power of hair styles which is a feature particularly desired by persons having fine hair or hair tending to oilness.

The compositions accordng to the present invention which are intended for the treatment of the skin impart thereto a soft and non-sticky feel and a non-oily appearance. These compositions are indeed penetrating, and have an emoillient effect that is to say, they soften and lubricate the skin and maintain its suppleness as well as protect it from atmospheric aggressions.

The cosmetic compositions according to the present invention can contain, in addition to the powder of sweet lupine seeds, conventional components for the type of composition considered (active components, vehicles and excipients).

Particularly preferred forms of the compositions according to the present invention, comprise a shampoo formulation and an after-shampoo composition which can contain, in addition to the powder of sweet lupine seeds, anionic, cationic, non-ionic or amphoteric surfactants, or mixtures thereof as well as thickening agents, preservatives, antioxidants, perfumes and coloring agents.

Generally in the capillary compositions of the present invention containing surfactants, the surfactant is preferably:

either a mixture of fatty alcohols, such as cetyl-stearyl alcohol, and polyoxyethylenated fatty alcohols such as cetyl-stearyl alcohol oxyethylenated with 2-30 moles of ethylene oxide including such commercially available products as "Sinnowax AO" sold by Henkel, which includes 80% of cetyl-stearyl alcohol and 20% cetyl-stearyl alcohol oxyethylenated with 33 moles of ethylene oxide, or at least one polyalkoxycarboxylic derivative of the formula, $R-(OCH_2CH_2)_n-O-CH_2-COOH$ wherein R is linear alkyl having 6-18 carbon atoms, preferably 12-18 carbon atoms, and n is a number ranging from 5-25, preferably from 5-10, the carboxylic group being able to be salified, principally in the form of its alkaline salts, sodium and potassium, or its ammonium salt, for example $NH_4^+$. Such surfactants are principally those sold by Sandoz under the mark "SANDOPAN DCT" acid (R=$C_{13}$ alkyl; n=7) or SANDOPAN LS 24" (R=$C_{12}$ alkyl; n=13; sodium salt). This latter product is also sold by Miranol under the trademark "MIRANATE LEC".

Generally, the surfactant is present in an amount ranging from 0.1 to 50 percent by weight, based on the total weight of the composition.

The compositions for application to the skin in the form of fluid emulsions or creams contain an oil phase emulsified with an aqueous phase in the presence of conventional components or adjuvants.

The present invention also relates to the use of the powder of sweet lupine seeds in the production of cosmetic or dermopharmaceutical compositions such as defined above.

The following non-limiting examples illustrate the present invention.

In these examples, the powder of white sweet lupine (lupinus albus) seeds employed is a powder having a granulometry lower than 80 μm.

EXAMPLE 1

An after-shampoo composition is prepared having the following composition:

| | |
|---|---|
| Powder of white sweet lupine seeds | 9.00 g |
| Stearic acid | 8.00 g |
| Cetyl alcohol | 0.90 g |
| Mixture of cetyl-stearyl alcohol and cetyl-stearyl alcohol oxyethylenated with 33 moles of ethylene oxide, sold under the name "SINNOWAX AO" by Henkel | 2.00 g |
| Petrolatum oil | 2.00 g |
| Propylene glycol | 9.50 g |
| Preservative, perfume, coloring agent, sufficient amount | |
| Water, sufficient amount for | 100 g |

This composition is applied, after a shampoo, to wet hair. After permitting the composition to remain in contact with the hair for a period of about 10 minutes the hair is rinsed.

After drying the rinsed hair, the hair is manageable, shiny and exhibits a good hold.

EXAMPLE 2

An after-shampoo composition is prepared having the followng composition:

| | |
|---|---|
| Powder of white seed lupine seeds | 3.00 g |
| Methyl glucose sesquistearate, sold under the name "GLUCATE SS" by Amerchol | 7.20 g |
| Sesquistearate of polythylene glycol ether (with 20 moles of ethylene oxide) and of methyl glucose, sold under the name "GLUCAMATE SSE.20" by Amerchol | 2.85 g |
| Preservative, perfume, coloring agent, sufficient amount | 100 g |

This composition is applied after a shampoo to wet hair and is permitted to remain in contact therewith for 10 minutes. Thereafter the hair is rinsed and dried and the thus treated hair is light and shiny and exhibits a good hold.

EXAMPLE 3

An after-shampoo composition in the form of a cream having the following composition is prepared:

| | |
|---|---|
| Powder of white sweet lupine seeds | 13.5 g |
| Turnsole oil | 38.5 g |
| Preservative, perfume, antioxidant, sufficient amount | |
| Water, sufficient amount for | 100 g |

This cream is applied after a shampoo to wet hair and is permitted to remain in contact therewith for 5 to 10 minutes. Thereafter the hair is thoroughly rinsed and dried. The thus treated hair exhibits a good hold and is very soft and shiny.

EXAMPLE 4

An after-shampoo composition is prepared having the following composition:

| | |
|---|---|
| Powder of white sweet lupine seeds | 6.5 g |
| Guar gum having a granulometry lower than 100 μm, sold under the name "VIDOGUM GH 175", by Unipektin AG | 1.75 g |
| Preservative, perfume, sufficient amount | |

| | |
|---|---|
| Water, sufficient amount for | 100 g |

This preparation is applied after shampooing to clean and wet hair and is permitted to remain in contact therewith for 15-20 minutes. The hair is then rinsed and dried. The thus treated hair exhibits good softness and suppleness and is also very shiny.

EXAMPLE 5

A shampoo composition is prepared having the following composition:

| | |
|---|---|
| Powder of white sweet lupine seeds | 11 g |
| Lauryl ether sulfate of monoethanolamine having 2 moles of ethylene oxide, in the form of an aqueous solution having 25% active material | 5 g |
| Colza oil | 30 g |
| Preservative, perfume, antioxidant, sufficient amount | |
| Water, sufficient amount for | 100 g |

The foam of this shampoo is unctuous and creamy and when rinsed and dried the hair is particularly supple and light.

EXAMPLE 6

A cream shampoo having the following composition is prepared:

| | |
|---|---|
| Powder of white sweet lupine seeds | 10 g |
| Lauryl ether sulfate of monoisopropanolamine, ethoxylated with 1-4 moles of ethylene oxide, sold under the name "TEXAPON WW 99" by Henkel | 20 g |
| Colza oil | 30 g |
| Preservative, perfume, antioxidant, sufficient amount | |
| Water, sufficient amount for | 100 g |

The foam of this shampoo is unctuous and creamy and when rinsed and dried the hair is particularly supple and light.

EXAMPLE 7

A shampoo having the following composition is prepared:

| | |
|---|---|
| Powder of white sweet lupine seeds | 14 g |
| Lauryl ether sulfate of monoethanolamine having 2 moles of ethylene oxide in the form of an aqueous solution of 25% active material | 5 g |
| Colza oil | 15 g |
| Preservative, antioxidant, perfume, sufficient amount | |
| Water, sufficient amount for | 100 g |

This shampoo provides a soft and light foam and when rinsed and dried the hair is shiny and the style imparted thereto exhibits a good hold.

EXAMPLE 8

A hand cream having the following conposition is prepared:

| | |
|---|---|
| Powder of white sweet lupine seeds | 15 g |
| Polyethylene glycol stearate, oxyethylenated with 20 moles of ethylene oxide, sold under the name "MYRJ 49" by Atlas | 6.6 g |
| Mono-and distearate of glycerol | 1.2 g |
| Cetyl alcohol | 4.2 g |
| Mixture of cetyl-stearyl alcohol and sodium alkyl sulfate, sold under the name "SINNOWAX SX" by Henkel | 4 g |
| Petrolatum oil | 5 g |
| Cyclic dimethyl polysiloxane, sold under the name "VOLATILE SILICONE 7158" by Union Carbide | 5 g |
| S—carboxymethyl cysteine | 1 g |
| Triethanolamine, sufficient amount for pH = 6.8 | |
| Preservative, coloring agent, perfume | 0.3 g |
| Water, sufficient amount for | 100 g |

This preparation is applied to the hands so that it penetrates the skin. The skin becomes smooth and very soft.

EXAMPLE 9

A face mask having the following composition is prepared:

| | |
|---|---|
| Powder of white sweet lupine seeds | 20 g |
| Propylene glycol | 12 g |
| Titanium Dioxide | 0.5 g |
| Hydroxyethyl cellulose, sold under the name "NATROSOL 250HHR" by Hercules | 0.7 g |
| Preservative, coloring agent, perfume | 0.2 g |
| Water, sufficient amount for | 100 g |

This preparation is applied to the face. After remaining in contact therewith for 5 to 10 minutes, the face is washed with lukewarm water and dried. The skin thus treated is soft, supple and smooth.

EXAMPLE 10

| | |
|---|---|
| Powder of white sweet lupine seeds | 5.0 g |
| Clay | 2.0 g |
| Sandopan DTC acid | 0.7 g |
| Xanthane gum | 1.8 g |
| Water, sufficient amount for | 100 g |

This preparation is applied after a shampoo to clean and wet hair. After remaining in contact therewith for 15-20 minutes, the hair is rinsed and dried. The thus treated hair exhibits good softness and suppleness and the hold of the hair style imparted thereto is excellent.

What is claimed is:

1. A topical composition for to the hair, skin and scalp, said composition being in the form of an emulsion, a cream, a lotion, a gel or a powder and comprising in a cosmetically acceptable vehicle, an effective amount of a powder of sweet lupine seeds essentially free of alkaloids.

2. The composition of claim 1 wherein said seeds are seeds of *Lupinus albus, Lupinus angustifolius, Lupinus polyphyllus* or *Lupinus luteus*.

3. The composition of claim 1 wherein said seeds are seeds of *Lupinus albus*.

4. The composition of claim 1 wherein said powder of sweet lupine seeds is present in an amount of at least 5 weight percent based on the total weight of said composition.

5. The composition of claim 1 wherein said powder of sweet lupine seeds has a granulometry lower than or equal to 125 µm.

6. The composition of claim 1 wherein at least 98 percent of the particles of said powder of sweet lupine seeds have a size lower than 80 µm.

7. The composition of claim 1 wherein said seeds are delipidated.

8. A topical cosmetic composition for to the hair, skin and scalp, said composition being in the form of an emulsion, a cream, a lotion, a gel or a powder and comprising in a cosmetically acceptable vehicle, an effective amount of a powder of sweet lupine seeds essentially free of alkaloids and from 0.1 to 50 weight percent, based on the total weight of said composition, of an anionic, cationic, amphoteric or non-ionic surfactant.

9. The composition of claim 8 wherein said surfactant is:
 (1) a mixture of a fatty alcohol and a polyoxyethylenated fatty alcohol,
 (2) a polyalkoxycarboxylic derivative of the formula, $R-(OCH_2CH_2)_n-O-CH_2-COOH$, wherein R is linear alkyl having 6-18 carbon atoms, and n is a number ranging from 5 to 25, or an alkali or ammmonium salt thereof.

10. A process for the treatment of the hair, skin or scalp comprising applying thereto an effective amount of the composition of claim 1.

* * * * *